United States Patent
Lin et al.

(10) Patent No.: US 10,183,040 B2
(45) Date of Patent: Jan. 22, 2019

(54) METHOD FOR REGULATION OF LIPID METABOLISM

(71) Applicant: PROFEAT BIOTECHNOLOGY CO., LTD., Taoyuan (TW)

(72) Inventors: Tsun-Yuan Lin, Taoyuan (TW); Hsun-Jin Jan, Taoyuan (TW); Chai-Hui Fu, Taoyuan (TW); Tsang-Tse Chen, Taoyuan (TW); Mu-Kuei Chen, Taoyuan (TW); Horng-Mo Lee, Taoyuan (TW)

( * ) Notice: Subject to any disclaimer, the term of this patent is extended or adjusted under 35 U.S.C. 154(b) by 0 days.

(21) Appl. No.: 15/122,441

(22) PCT Filed: Dec. 1, 2014

(86) PCT No.: PCT/CN2014/092688
§ 371 (c)(1),
(2) Date: Aug. 30, 2016

(87) PCT Pub. No.: WO2016/086338
PCT Pub. Date: Jun. 9, 2016

(65) Prior Publication Data
US 2017/0224727 A1    Aug. 10, 2017

(51) Int. Cl.
*A61K 33/26* (2006.01)
*A61K 31/198* (2006.01)
*A61K 9/08* (2006.01)
*A61K 9/20* (2006.01)
*A61K 9/48* (2006.01)

(52) U.S. Cl.
CPC ............ *A61K 33/26* (2013.01); *A61K 9/08* (2013.01); *A61K 9/20* (2013.01); *A61K 9/48* (2013.01); *A61K 31/198* (2013.01)

(58) Field of Classification Search
None
See application file for complete search history.

(56) References Cited

U.S. PATENT DOCUMENTS

2003/0050341 A1    3/2003    Bydlon et al.
2003/0206969 A1    11/2003   Nidamarty et al.

FOREIGN PATENT DOCUMENTS

| CN | 101102762 A | 1/2008 |
| CN | 101129351 A | 2/2008 |
| GB | 802565 A    | 10/1958 |

OTHER PUBLICATIONS

Anonyous, Ferrous bisglycinate, ChemIDplus, Accessed Dec. 10, 2017 (2017).
EP14907194—European Search Report dated Oct. 24, 2017.

*Primary Examiner* — Kevin S Orwig
*Assistant Examiner* — Barbara S Frazier (57) ABSTRACT

Provided is a method for regulation of lipid metabolism comprising a step of administering to a subject in need thereof a therapeutically amount of pharmaceuticals. The pharmaceuticals comprise an effective amount of a composition containing a ferrous amino acid chelate and pharmaceutically acceptable carriers to regulate lipid metabolism. The amino acid is capable of being chelated with the ferrous iron in a chelated state stably as passing through a stomach. The composition containing the ferrous amino acid chelate can effectively control the variances of body weight and enhance metabolism of body fat of a subject. The pharmaceuticals prepared by the composition containing the ferrous amino acid chelate have effects on regulation of lipid metabolism.

9 Claims, 6 Drawing Sheets

METHOD FOR REGULATION OF LIPID METABOLISM

BACKGROUND OF THE INVENTION

1. Field of the Invention

The present invention relates to a method for regulation of lipid metabolism, especially to the method for regulation of lipid metabolism by administering to a subject with a composition containing a ferrous amino acid chelate.

2. Description of the Prior Art

Metabolic syndrome is a disease of civilization caused by lifestyle habits (Lupatini et al., 2008) and dietary habits (Esoisuti et al., 2007) of modern people. According to the definition defined by the World Health Organization (WHO) in 1998, a person who has a syndrome of impaired glucose tolerance or insulin resistance, and additional two syndromes of hypertension, obesity, dyslipidemia or microalbuminuria can be diagnosed as suffering the metabolic syndrome. In Taiwan, a person who has three of the following five conditions is diagnosed as having metabolic syndrome. The five conditions include that (1) the waist circumference of male is greater than or equal to 90 cm, and the waist circumference of female is greater than or equal to 80 cm; (2) the triacylglycerol is greater than 150 mg/dl; (3) the high density lipoprotein (HDL) of male is less than 40 mg/dl, and the HDL of female is less than 50 mg/dl; (4) the systolic blood pressure is higher than 130 mmHg, and the diastolic blood pressure is higher than 85 mmHg, and (5) the value of fasting blood glucose is greater than 110 mg/dl. The rate of suffering from metabolic syndrome of Taiwanese is increasing with age, and many diseases among the top ten causes of death are related to the metabolic syndrome. The average life expectancy of patients with metabolic syndrome is shorter than normal persons. The reason is that the cardiovascular disease caused by high blood pressure or hyperlipidemia, or the diabetes caused by insulin resistance will cause acute complications.

SUMMARY OF THE INVENTION

For the shortcomings of the side effects caused by treatment with conventional chemical pharmaceuticals, the objective of the present invention is to provide a method for regulation of lipid metabolism comprising administering to a subject in need thereof a therapeutically effective amount of pharmaceuticals, wherein the pharmaceuticals comprises an effective amount of a composition containing a ferrous amino acid chelate and pharmaceutically acceptable carriers.

According to the present invention, the term "the composition containing the ferrous amino acid chelate" refers to the composition made by mixing an inorganic iron with an amino acid.

Preferably, the inorganic iron comprises, but is not limited to, ferrous sulfate, ferrous chloride, or ferrous pyrophosphate, and the amino acid is glycine.

More preferably, the composition containing the ferrous amino acid chelate comprises 95% to 100% weight percentage of the ferrous glycine chelate. Furthermore preferably, the composition containing the ferrous amino acid chelate comprises 98% to 99.9% weight percentage of the ferrous glycine chelate.

Preferably, the composition containing the ferrous amino acid chelate is prepared from mixing ferrous sulfate with glycine followed by heating between 60° C. and 90° C. for 8 hours to 48 hours, wherein a weight ratio of the ferrous sulfate to the glycine of ferrous amino acid chelate is between 1:1.2 and 1:1.5.

The composition containing the ferrous amino acid chelate in accordance with the present invention comprises at least one ferrous amino acid chelate, and the chelating ratio of the ferrous iron to the amino acid of the composition containing the ferrous amino acid chelate is between 1:1 and 1:4. More preferably, the chelating ratio of the ferrous iron to the amino acid of the composition containing the ferrous amino acid chelate is between 1:1.5 and 1:2.5.

Preferably, the composition containing the ferrous amino acid chelate comprises a reducing agent. The reducing agent can maintain the oxidation state of the ferrous iron of the ferrous amino acid chelate contained in the composition. Besides, the reducing agent can also enhance the intestinal absorption rate of the composition containing the ferrous amino acid chelate in subjects. The reducing agent comprises, but is not limited to ascorbic acid, citric acid, acetic acid, propionic acid, butyric acid, lactic acid, malic acid, sulfonic acid or succinic acid.

According to the present invention, the term "lipid metabolism" in accordance with the present invention means effectively treating or relieving blood lipid disorder. The regulation of lipid metabolism comprises, but is not limited to reducing lipid synthesis and enhancing fatty acid metabolism. As shown in the embodiment of the present invention, regulation of lipid metabolism means body weight control, body fat loss, and regulation of triacylglycerol.

According to the present invention, the term "effective amount" in accordance with the present invention means dosage of the pharmaceuticals used for effective regulation of lipid metabolism in the required period. As shown in the embodiment of the present invention, the dosage of the pharmaceuticals used for effective regulation of lipid metabolism can be determined by administering the composition containing the ferrous amino acid chelate in a specific amount, and measuring the body weight, serum biochemical values and body fat in a specific period.

According to the present invention, the term "serum biochemical values" in accordance with the present invention comprises, but is not limited to triacylaglycerol, cholesterol, low density lipoprotein, and high density lipoprotein.

Preferably, the effective amount of the composition containing the ferrous amino acid chelate is between 0.1 mg/kg/day and 5 mg/kg/day. More preferably, the effective amount is between 0.16 mg/kg/day and 4 mg/kg/day.

According to the present invention, the term "pharmaceutically acceptable carriers" in accordance with the present invention comprises any of physiologically compatible solvents, dispersed medium, coating materials, antibacterial agents, antifungal agents, isotonic agents, and absorption delaying and analogues thereof. The pharmaceutically acceptable carriers comprise water, saline, phosphate buffered solution, dextrose, glycerol, ethanol, analogues thereof or any combination thereof. In many conditions, preferably, the pharmaceutically acceptable carriers comprise isotonic agents, for example, sugars, polyalcohols such as mannitol and sorbitol, or sodium chloride. The pharmaceutically acceptable carriers can further comprise micro-auxiliary substances such as wetting agent, emulsifier, preservative or buffering agent.

The pharmaceuticals in accordance with the present invention comprise various dosage forms, and the dosage form comprises, but is not limited to liquid, semi-solid and solid. The liquid comprises, but is not limited to dispersion or suspension. The semi-solid and the solid dosage forms comprise, but are not limited to tablet, pill, powder, liposome or suppository. The preferred dosage form of the pharmaceuticals is dependent on the expected mode of administration and therapeutic application.

Preferably, the dosage form of the pharmaceuticals in accordance with the present invention is for oral dosage administration or injection. The preferred mode of administration is the mode of enteral administration, such as oral administration. As shown in the embodiment of the present invention, the pharmaceuticals comprising the composition containing the ferrous amino acid chelate for effective regulation of lipid metabolism are orally administered.

Preferably, the pharmaceuticals further comprise an excipient, allowing the pharmaceuticals to be made in the dosage form applicable to enteral administration or parenteral administration.

Preferably, the dosage form of the pharmaceuticals for enteral administration is oral dosage form. The oral dosage form comprises, but is not limited to solution, suspension, tablet or capsule.

The composition containing the ferrous amino acid chelate in accordance with the present invention has effects on regulation of lipid metabolism. Besides, for the reason that the molecular weight of the amino acid is small enough to be chelated with the ferrous iron in a chelating state stably as passing through a stomach of a subject, the composition containing the ferrous amino acid chelate can effectively control body weight of the subject and enhance lipid metabolism and lipolysis.

BRIEF DESCRIPTION OF THE DRAWINGS

FIG. 5A to 5D are histochemical staining assays of body fat deposition in livers of mice administered with composition A1 for 12 weeks, wherein FIG. 5A is the control group recited in Table 1 (feeding mice with fixed amount of high fat diet); FIG. 5D is the composition A1 with high dose group recited in Table 1 (feeding mice with any amount of high fat diet and administering mice with 1.2 mg/kg composition A1 for 12 weeks).

DETAILED DESCRIPTION OF THE PREFERRED EMBODIMENTS

Preparation Example 1: Preparation of the Composition Containing a Ferrous Amino Acid Chelate The method for preparing a composition containing a ferrous amino acid chelate was shown as follows. First, ferrous sulfate was mixed with glycine (above 98% purity) at a weight ratio of 1:1.3 followed by heating from 60° C. to 90° C. for 8 hours to 48 hours to form the composition containing the ferrous amino acid chelate. The chelating ratio of ferrous iron to amino acid of the ferrous amino acid chelate was between 1:1 and 1:4. The composition containing the ferrous amino acid chelate was prepared in concentrations of 1 μg/ml, 3 μg/ml, 10 μg/ml, and 30 μg/ml. The composition containing the ferrous amino acid chelate was named as composition A1.

Preparation Example 2: Animal Study

C57BL/6JNR male mice at 12 weeks of age (50 g body weight per mouse) and db/db male mice at 14 weeks of age (55 g body weight per mouse) (purchased from National Laboratory Animal Center) were fed under 12/12-hour light-dark cycle and supplied with water.

TABLE 1

| Groups | Control group | Composition A1 with low dose group | Composition A1 with high dose group | Composition A1 with high dose group |
|---|---|---|---|---|
| Number of mice | 10 | 5 | 5 | 5 |
| Mice strain | C57BL/6JNR | C57BL/6JNR | C57BL/6JNR | C57BL/6JNR |
| Sex | Male | Male | Male | Male |
| Diet | High fat diet | High fat diet | High fat diet | High fat diet |
| Feed amount (g) | 2.2 | 2.2 | 2.2 | Any amount |
| Composition A1 (mg/kg) | 0 | 0.4 | 1.2 | 1.2 |
| Age (weeks) | 10 | 10 | 10 | 10 |
| Induction period (weeks) | 4 | 4 | 4 | 4 |
| Body weight (g) | 23 | 23 | 23 | 23 |
| Feeding period (weeks) | 12 | 12 | 12 | 12 |

TABLE 2

| Groups | Control group | Experimental group |
|---|---|---|
| Number of mice | 5 | 5 |
| Mice strain | C57BLKS/J-leprdb/leprdb | C57BLKS/J-leprdb/leprdb |
| Sex | Male | Male |
| Diet | High fat diet | High fat diet |
| Feed amount (g) | 3.5 | 3.5 |
| Pharmaceuticals | — | Composition A1 (12 mg/kg) |
| Age (weeks) | 12 to 14 | 12 to 14 |
| Body weight (g) | 45 | 45 |
| Feeding period (weeks) | 13 | 13 |

TABLE 3

| Groups | Control group | Comparison group | Composition A1 with low dose group | Composition A1 with high dose group |
|---|---|---|---|---|
| Number of mice | 10 | 5 | 5 | 5 |
| Diet | Normal | High fat diet | High fat diet | High fat diet |
| Composition A1 (mg/kg) | 0 | 0 | 0.16 | 0.4 |

TABLE 4

| Groups | Control group | Comparison group 1 | Comparison group 2 | Experimental group |
|---|---|---|---|---|
| Number of mice | 5 | 5 | 5 | 5 |
| Mice strain | C57BLKS/J-leprdb/leprdb | C57BLKS/J-leprdb/leprdb | C57BLKS/J-leprdb/leprdb | C57BLKS/J-leprdb/leprdb |
| Pharmaceuticals | Phosphate solution | Commercial ferrous glycine (4 mg/kg/day) | Ferrous sulfate (4 mg/kg/day) | Composition A1 (4 mg/kg/day) |

The mice were divided into groups as shown in Table 1 and Table 2. The mice were daily and orally administered with the composition A1 at dosage of 0.4 mg/kg/day and 1.2 mg/kg/day for 12 weeks. The body weights of the mice were measured every 3 days, and the serum biochemical values of the mice were measured every 4 weeks after orally administering with the composition A1. Triacylglycerol and cholesterol of the serum biochemical values were determined using a Biochem-Immuno Fully Autoanalyzer (Brea, Calif., USA) or a Chemistry Analyzer (Hitachi, Ltd., Japan). The mice were sacrificed after administering with the composition A1 for 3 months, and the body fat deposited in abdomen and livers of the mice as well as the body weights were observed.

Preparation Example 3: Histochemical Staining Analysis

Mice of the preparation example 2 were sacrificed, and the livers of mice were fixed by use of the frozen section compound (Leica Microsystems, Germany) to form a frozen tissue segment, and the frozen tissue segment was kept at −80° C. The frozen tissue segment was sliced up into slices by use of a freezing microtome, and the thickness of each of the slices was 7 μm. Each of the slices was stained on a slide to form a sample with Hematoxylin and Eosin, oil red or Sudan III respectively. The methods for staining were shown as follows.

1. Hematoxylin and Eosin Staining
   (1) the sample was stained with hematoxylin solution for 5 minutes;
   (2) the stained sample was washed with water followed by immersing into ammonia water (2 drops of stronger ammonia water in 1000 ml water) for a few seconds till the tissue became blue;
   (3) the washed sample was washed with water followed by staining with 0.5% eosin solution for a few seconds;
   (4) the washed sample was sequentially washed with 70% ethanol, 95% ethanol and 100% ethanol;
   (5) the washed sample was sequentially immersed in xylene-100% ethanol solution (1:1), xylene-creosote (4:1), xylene (I) and xylene (II) each for half minute; and,
   (6) each of the immersed samples was allowed to become transparent by use of xylene, and each of the samples was sealed after 2 minutes.

2. Oil Red Staining
   (1) each of the samples was washed with distilled water for a short time;
   (2) each of the washed samples was immersed in 50% isopropyl alcohol;
   (3) each of the immersed samples was stained with oil red solution for 10 minutes to 15 minutes;
   (4) each of the stained samples was washed with water;
   (5) each of the washed samples was counterstained with Mayer hematoxylin solution for 3 minutes;
   (6) each of the counterstained samples was washed with water for 15 minutes; and,
   (7) the washed samples were sealed with glycerin jelly as each of the washed samples became hemi-dry.

3. Sudan III Staining
   (1) each of the samples was washed with distilled water;
   (2) each of the washed samples was immersed in 50% alcohol;
   (3) each of the immersed samples was stained with 37° C. Sudan III-Alcohol solution for 1 hour;
   (4) each of the stained samples was slightly washed with 50% alcohol to remove the residue staining solution;
   (5) each of the washed samples was slightly washed with water for 20 minutes; and (6) each of the washed samples was sealed with glycerol or glycerin jelly as each of the samples became hemi-dry.

Example 1: Examination of the Effect on Mice Body Weight after Administration of Composition A1

Figure 1A:
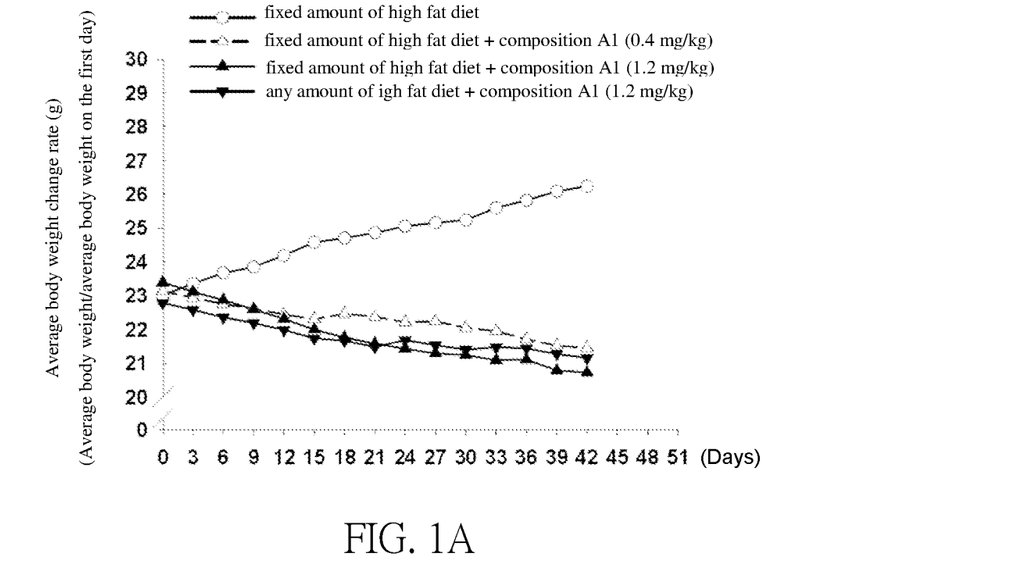
FIG. 1A is a curve chart of the average body weight change rate (g) measured every 3 days of mice respectively orally administered with 0.4 mg/kg and 1.2 mg/kg of the composition A1 for 12 weeks in accordance with the present invention.
Figure 1B:
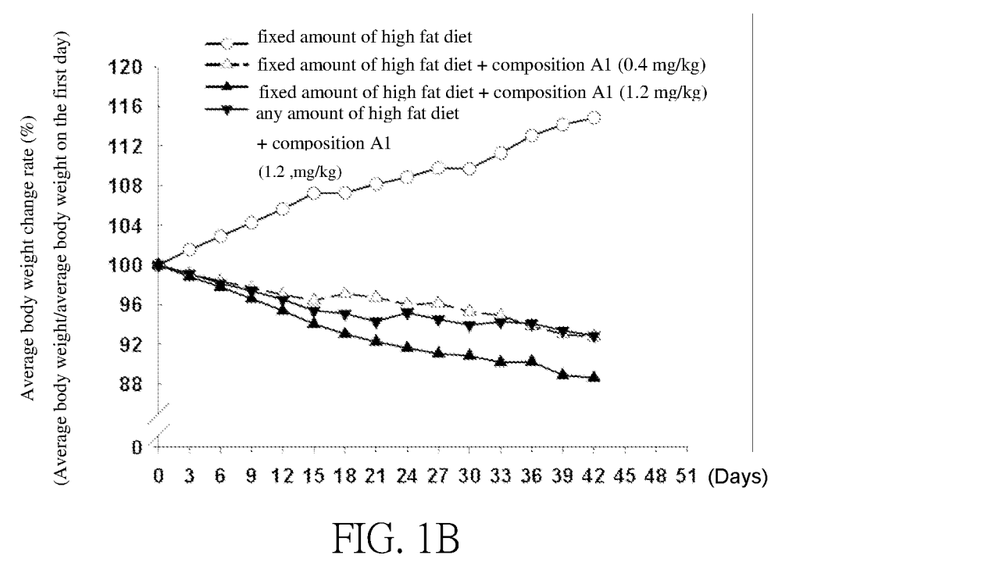
FIG. 1B is a curve chart of the average body weight change rate (%) weighted every 3 days of mice respectively orally administered with 0.4 mg/kg and 1.2 mg/kg of the composition A1 for 12 weeks in accordance with the present invention.

As shown in Table 1 of preparation example 2, the average body weight and the average body weight change rate were measured every 3 days of mice respectively orally administered with 0.4 mg/kg and 1.2 mg/kg of the composition A1 for 12 weeks. The results were shown in FIGS. 1A and 1B; the body weight of the mice was effectively lost by administering composition A1.

As shown in Table 2 of preparation example 2, db/db mice were congenital genetic deficient mice with lack of leptin receptor gene, and the mice spontaneously suffered type 2 diabetes at 8 weeks to 10 weeks of age. Once the mice suffered type 2 diabetes, the mice were orally administered with 1.2 mg/kg composition A1 for 12 weeks. The average body weight and the average body weight change rate of the mice were measured every 3 days.

Figure 2A:
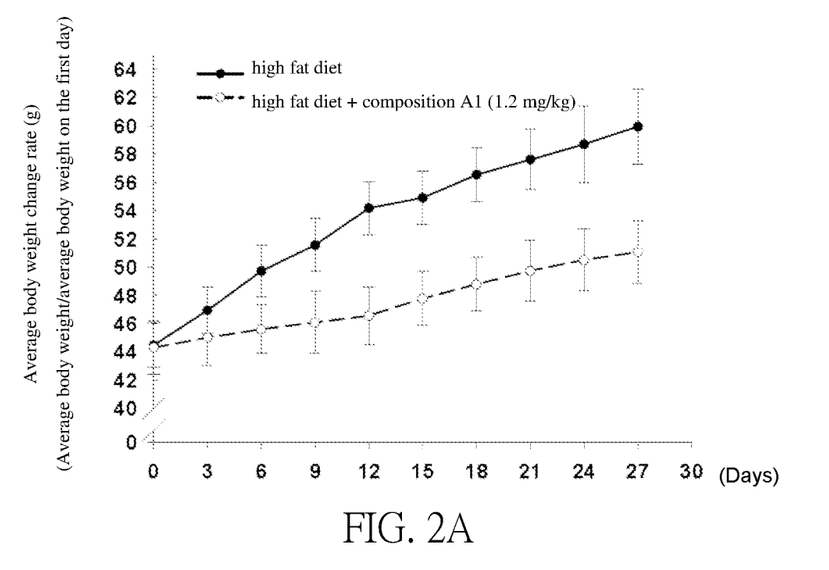
FIG. 2A is a curve chart of the average body weight change rate (g) weighted every 3 days of mice orally administered with 1.2 mg/kg of the composition A1 for 1 month in accordance with the present invention.
Figure 2B:
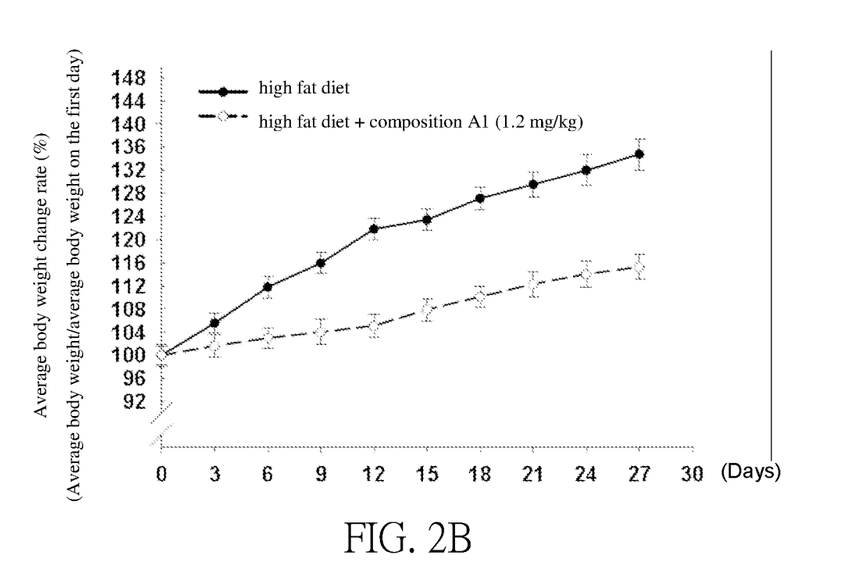
FIG. 2B is a curve chart of the average body weight change rate (%) weighted every 3 days of mice orally administered with 1.2 mg/kg of the composition A1 for 1 month in accordance with the present invention.

The results were shown in FIGS. 2A and 2B; the body weights of the mice in the control group (without administering any pharmaceutical) were stably increased. The body weights of the mice administered with composition A1 were lower than those of the mice in the control group. As shown in the results of FIG. 2B, the body weight of the mice in the control group were increased by about 34% in one month; whereas the body weight of the mice administered with composition A1 were increased by only 22%. Therefore, composition A1 was effectively used in regulation of body weight.

Example 2: Examination of the Effects on Mice Serum Biochemical Values and Body Fat after Administration of Composition A1

Figure 3A:
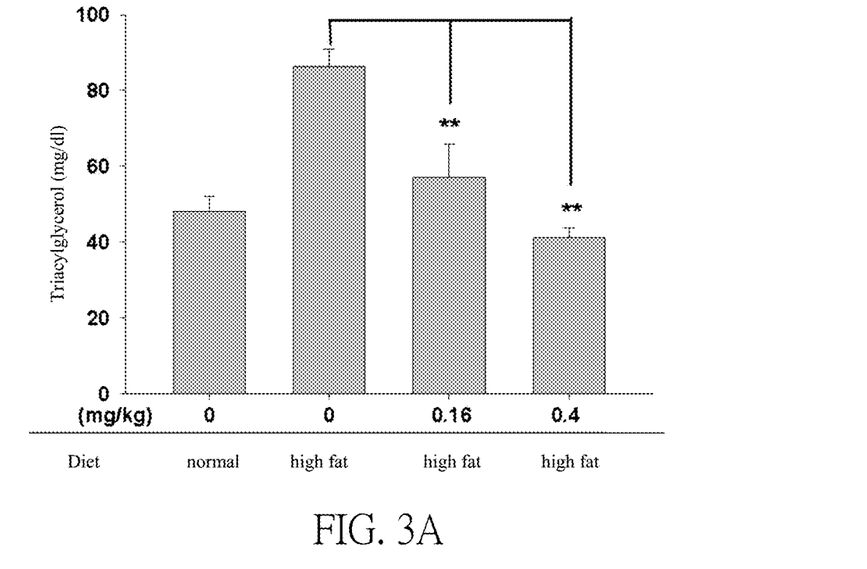
FIG. 3A is a bar chart of the triacylglycerol assay of high fat diet mice orally administered with 0.16 mg/kg or 0.4 mg/kg composition A1 for 12 weeks in accordance with the present invention.

As shown in Table 3 of preparation example 2 and FIG. 3A, triacylglycerol were respectively reduced by 33% and by 50% of the high fat diet mice administered with 0.16 mg/kg and 0.4 mg/kg composition A1 and the high fat diet mice (as well as the control group). Besides, after administering the high fat diet mice with 0.4 mg/kg composition A1, the triacylglycerol of the mice was approximately equal to that of the mice fed with normal diet (as well as the control group). The results showed that the composition A1 effectively reduced tiracylglycerol of the obese mice caused by high fat diet.

Figure 3B:
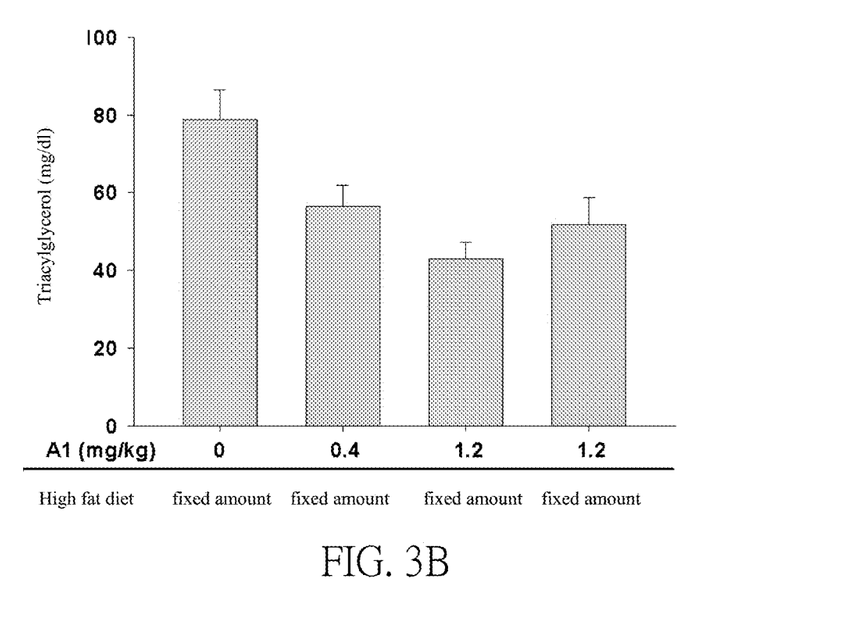
FIG. 3B is a bar chart of the triacylglycerol assay of fixed amount or any amount of high fat diet fed mice orally administered with 0.4 mg/kg or 1.2 mg/kg composition A1 for 12 weeks in accordance with the present invention.

As shown in Table 1 of preparation example 2, the serum biochemical values were measured every 3 days of the mice respectively orally administered with 0.4 mg/kg and 1.2 mg/kg of the composition A1 for 12 weeks. The results were shown in FIG. 3B, triacylglycerol was respectively reduced by 30% and 45% of the fixed amount of high fat diet mice administered with 0.4 mg/kg and 1.2 mg/kg composition A1 and the mice of the control group. Besides, the reduction degrees of triacylglycerol of any amount of high fat diet mice administered with 1.2 mg/kg composition A1 was similar to that of fixed amount of high fat diet mice administered with 0.4 mg/kg composition A1.

Figure 4A:
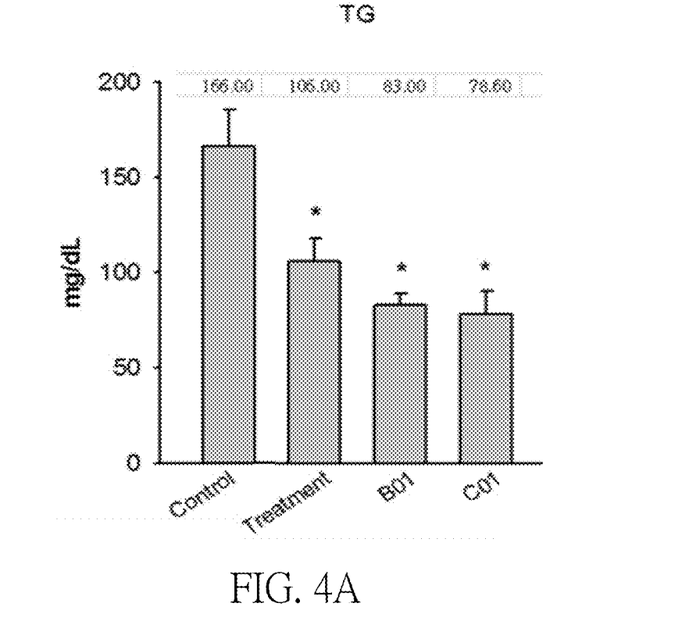
FIG. 4A is a bar chart of the triacylglycerol assay of diabetes mice in accordance with the present invention, wherein the mice of control group are administered with phosphate buffer; the mice of treatment group are administered with 4 mg/kg/day composition A1; the mice of B01 group are administered with commercial 4 mg/kg/day ferrous glycine, and the mice of C01 group are administered with 4 mg/kg/day ferrous sulfate.
Figure 4B:
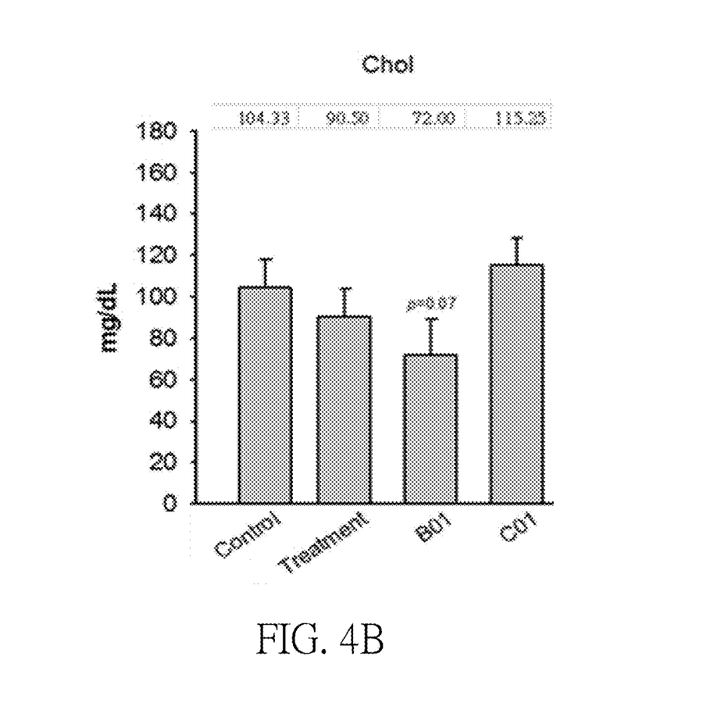
FIG. 4B is a bar chart of the cholesterol assay of diabetes mice in accordance with the present invention, wherein the mice of control group are administered with phosphate buffer; the mice of treatment group are administered with 4 mg/kg/day composition A1; the mice of B01 group are administered with commercial 4 mg/kg/day ferrous glycine, and the mice of C01 group are administered with 4 mg/kg/day ferrous sulfate.
Figure 4C:
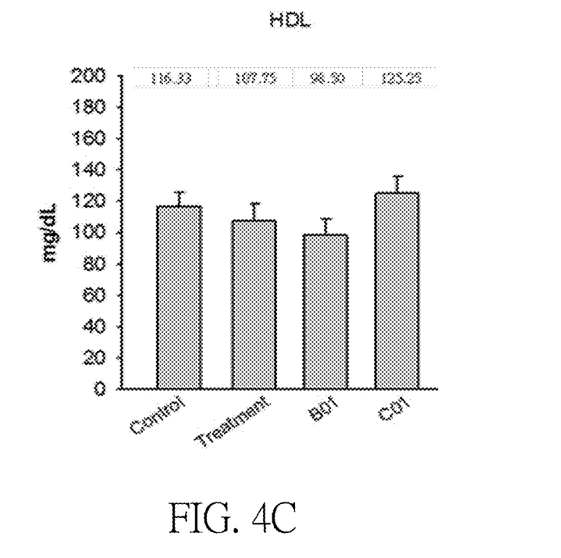
FIG. 4C is a bar chart of the high density lipoprotein (HDL) assay of diabetes mice in accordance with the present invention, wherein the mice of control group are administered with phosphate buffer; the mice of treatment group are administered with 4 mg/kg/day composition A1; the mice of B01 group are administered with commercial 4 mg/kg/day ferrous glycine, and the mice of C01 group are administered with 4 mg/kg/day ferrous sulfate.
Figure 4D:
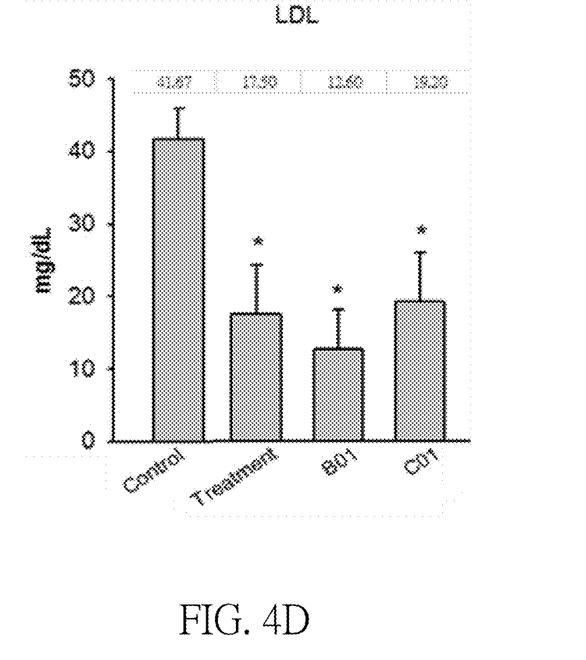
FIG. 4D is a bar chart of the low density lipoprotein (LDL) assay of diabetes mice in accordance with the present invention, wherein the mice of control group are administered with phosphate buffer; the mice of treatment group are administered with 4 mg/kg/day composition A1; the mice of B01 group are administered with commercial 4 mg/kg/day ferrous glycine, and the mice of C01 group are administered with 4 mg/kg/day ferrous sulfate.

As shown in Table 4 of preparation example 2, the mice of control group were administered with phosphate solution; the mice of comparison group 1 were administered with 4 mg/kg/day commercial ferrous glycine; the mice of comparison group 2 were administered with 4 mg/kg/day commercial ferrous sulfate, and the mice of experimental group were administered with 4 mg/kg/day composition A1. As shown in FIG. 4A, triacylglycerol was effectively reduced in comparison group 1 (B01, administered with commercial ferrous glycine), comparison group 2 (C01, administered with commercial ferrous sulfate) and experimental group (treatment, administered with composition A1). As shown in FIG. 4B, the concentration of cholesterol in each group was not reduced as the reduction results of triacylglycerol. Although the reduction effect was not obvious in FIG. 4C, FIG. 4D showed that low density lipoprotein (LDL) was reduced by about 58% in the experimental group as compared to the control group.

Example 3: Examination of the Effects on Mice-Tissue Lipid Disposition after Administration of Composition A1

Figure 5A:
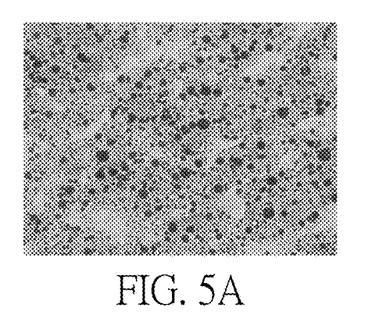
Figure 5B:
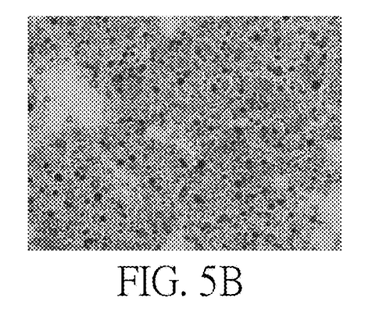
FIG. 5B is the composition A1 with low dose group recited in Table 1 (feeding mice with fixed amount of high fat diet and administering mice with 0.4 mg/kg composition A1 for 12 weeks)
Figure 5C:
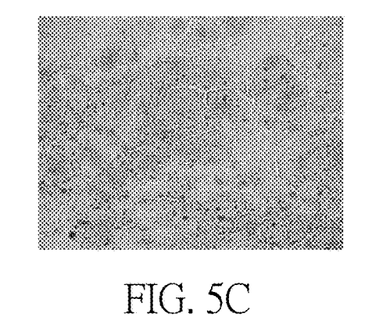
FIG. 5C is the composition A1 with high dose group recited in Table 1 (feeding mice with fixed amount of high fat diet and administering mice with 1.2 mg/kg composition A1 for 12 weeks)
Figure 5D:
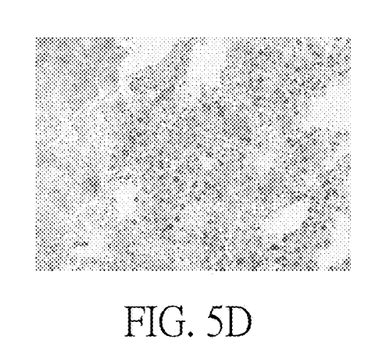

According to the staining method recited in preparation example 3, FIG. 5A was the comparison group (feeding mice with fixed amount of high fat diet). FIG. 5B showed that the lipid drops in the liver tissue were slightly reduced in the mice fed with fixed amount of high fat diet mice after administering with 0.4 mg/kg composition A1. FIGS. 5C and 5D respectively showed that the lipid drops in the liver tissue were also reduced in the mice fed with fixed amount of high fat diet mice and in the mice fed with any amount of high fat diet mice after administering with 1.2 mg/kg composition A1.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for regulation of lipid metabolism comprising: administering to a subject in need thereof a therapeutically effective amount of a composition consisting of a ferrous glycine chelate and pharmaceutically acceptable carriers.

2. The method as claimed in claim 1, wherein the chelating ratio of ferrous iron to the glycine of the composition consisting of the ferrous glycine chelate and the pharmaceutically acceptable carriers is between 1:1 and 1:4.

3. The method as claimed in claim 1, wherein the chelating ratio of ferrous iron to the glycine of the composition consisting of the ferrous glycine chelate and the pharmaceutically acceptable carriers is between 1:1.5 and 1:2.5.

4. The method as claimed in claim 1, wherein the therapeutically effective amount of the composition consisting of the ferrous glycine chelate and the pharmaceutically acceptable carriers is between 0.1 mg/kg/day and 5 mg/kg/day.

5. The method as claimed in claim 1, wherein the therapeutically effective amount of the composition consisting of the ferrous glycine chelate and the pharmaceutically acceptable carriers is between 0.16 mg/kg/day and 4 mg/kg/day.

6. The method as claimed in claim 1, wherein the composition consisting of the ferrous glycine chelate and the pharmaceutically acceptable carriers is prepared from mixing an inorganic iron with the glycine followed by heating between 60° C. and 90° C. for 8 hours to 48 hours, wherein the ratio of the inorganic iron to the glycine is between 1:1.2 and 1:1.5.

7. The method as claimed in claim 6, wherein the inorganic iron is ferrous sulfate, ferrous chloride, or ferrous pyrophosphate.

8. The method as claimed in claim 1, wherein a dosage form of the composition is for enteral administration or parenteral administration.

9. The method as claimed in claim 8, wherein the dosage form of the composition for enteral administration is oral dosage form, wherein the oral dosage form comprises solution, suspension, tablet or capsule.

* * * * *